United States Patent
Lee

(10) Patent No.: US 9,597,383 B2
(45) Date of Patent: *Mar. 21, 2017

(54) FORMULATION AND METHOD FOR PREPARING SPECIFIC T CELL, AND METHOD FOR PREPARING THE FORMULATION

(71) Applicant: FULLHOPE BIOMEDICAL CO., LTD., New Taipei (TW)

(72) Inventor: Jan Mou Lee, Taipei (TW)

(73) Assignee: FULLHOPE BIOMEDICAL CO., LTD., New Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 14/870,961

(22) Filed: Sep. 30, 2015

(65) Prior Publication Data
US 2016/0074490 A1    Mar. 17, 2016

Related U.S. Application Data

(63) Continuation-in-part of application No. 13/918,762, filed on Jun. 14, 2013, now abandoned.

(30) Foreign Application Priority Data

Jul. 5, 2012 (TW) .............................. 101124293 A

(51) Int. Cl.
| | |
|---|---|
| *C12N 5/00* | (2006.01) |
| *C12N 5/02* | (2006.01) |
| *A61K 39/00* | (2006.01) |
| *C12N 5/0783* | (2010.01) |

(52) U.S. Cl.
CPC ........ *A61K 39/0011* (2013.01); *C12N 5/0636* (2013.01); *A61K 2039/5158* (2013.01); *A61K 2039/572* (2013.01); *C12N 2501/2312* (2013.01); *C12N 2501/2315* (2013.01); *C12N 2502/1121* (2013.01); *C12N 2502/1164* (2013.01)

(58) Field of Classification Search
None
See application file for complete search history.

(56) References Cited

U.S. PATENT DOCUMENTS

2012/0219504 A1    8/2012    Cho et al.

OTHER PUBLICATIONS

Jun., 2007, J. Clin. Invest. vol. 117: 1466-1476.*
Himoudi et al., 2009, Canc. Res. vol. 69: 6598-606.*
Birkholz et al., 2010, Blood vol. 116: 2277-2285.
Lin et al., 2004, Ped. Aller. Immunol. vol. 15: 795-85.
ProMix 2013 CEF peptide pool, product sheet, pp. 1-2.
Lazana et al., 2012, Cell Therp. Immunother. vol. 97: 1338-1347.
Burt et al., 2008, Human Immunol. vol. 69: 469-74.

* cited by examiner

*Primary Examiner* — Amy Juedes
(74) *Attorney, Agent, or Firm* — WPAT, PC; Justin King; Douglas A. Hosack

(57) ABSTRACT

The present invention provides a formulation and method for preparing specific T cells, and a method for fabricating the formulation is also disclosed. The formulation can induce specific T cell responses, and comprises at least a cell population of dendritic killer cells presenting specific antigens. In addition, the method mentioned above for preparing specific T cells comprises following steps. A T cell population is provided, and then a formulation of preparing specific T cells is mixing with the T cell population. After cultivating, the specific T cells are harvested. Furthermore, the method for fabricating the above formulation comprises the following steps. First, a cell population of dendritic killer cells is provided. A target sample is then provided, and a step of making the cell population of the dendritic killer cells is co-cultivated with the target sample. After co-cultivating, a cell population of dendritic killer cells presenting specific antigens is harvested.

14 Claims, 17 Drawing Sheets

FORMULATION AND METHOD FOR PREPARING SPECIFIC T CELL, AND METHOD FOR PREPARING THE FORMULATION

CROSS-REFERENCE TO RELATED APPLICATIONS

This Non-provisional application is a continuous-in-part application claiming priority benefit from U.S. application Ser. No. 13/918,762 and claims priority under 35 U.S.C. §119(a) on Patent Application No(s). 101124293 filed in Taiwan, Republic of China, Jul. 5, 2012, the entire contents of which are hereby incorporated by reference.

FIELD OF THE INVENTION

This invention relates to a formulation/method for preparing specific T cells and a method for preparing the above formulation, especially relates to a formulation/method for preparing specific T cells and a method for preparing the above formulation by utilizing dendritic killer cells which can present specific antigens to induce T cells response.

BACKGROUND OF THE INVENTION

Human body will recognize the extraneous matter and start a series of defending process. This defense system is named as immune system. There are many different cells such as leukocytes and lymphocyte, and different protein factors such as immunoglobulins and cytokines working coordinately to protect the body. The immune systems are traditionally divided into innate and adaptive immune systems. Innate immune system is including soluble complement system, polymorphonuclear neutrophils, macrophages and natural killer cells. Adaptive immune system is including humoral and cellular immunity. Humoral immunity as well as cellular immunity involves lymphocyte, lymphokine and immunological memory system. The long-lasting immune memory mounts quick and strong immune responses towards the same pathogen which has invaded the body.

Immune system may respond to different pathogens due to the diversity of major histocompatibility complex (MHC) molecules. The endogenous and exogenous antigens derived from pathogens, are assembled with MHC molecules on the surface of antigen-presenting cells (APC) and then presented to T cells expressing corresponding T cell receptors. MHC in the human beings can be called Human Leukocyte Antigen, HLA, which can be categorized into class I, class II, and class III. HLA class I is widely expressed on all the somatic cells but Class II distribution is restricted to macrophages, B cells and dendritic cells.

Dendritic cells (DC), which have the broadest range of antigen presentation, are professional APC, and named by the appearance of dendrites extending from the cell body. DCs reside in the periphery of body as immature DCs (imDCs). Once pathogen invades human bodies, imDCs capture pathogen-derived antigens, migrate to draining lymph nodes to become mature DCs (mDCs), and present antigens to corresponding T cells there. Therefore, dendritic cells are the starter of the pathogen-specific cellular immune responses.

Natural killer (NK) cells, a key player of innate immune system, spontaneously kill cancer cells or virally infected cells prior to activation. Mechanisms underlying cytotoxicity of NK cells are grouped into two parts: a) interaction of cell surface tumor necrosis factor superfamily members and their receptors which leads to apoptosis of target cells, (b) release of soluble perforin and granzymes. NK cells are rich with small granules in their cytoplasm contain special proteins such as perforin and proteases known as granzymes. Upon release in close proximity to a cell slated for killing, perforin forms pores in the cell membrane of the target cell through which the granzymes and associated molecules can diffuse in, leading to destruction of target cells. Once virally infected cells or cancer cells have been killed, viral genomic content (CpG or poly I:C), cellular metabolites, and bystander cytokines such as IFN-•, IL-12 and TNF-•• would further activate and augment NK cell activity in term of cytotoxicity and effector cytokine production. Therefore NK cells serve as key innate effector cells targeting to virally infected cells and cancer cells in a non-antigen specific manner while DCs in adaptive immune system trigger antigen-specific cytotoxic T cells which can further clear the infection. Patients deficient in NK cells are proved to be highly susceptible to early phases of herpes virus infection.

Interferon-producing killer dendritic cells (IKDCs), a recently identified leukocyte population in mice, express phenotypes of non-T (CD3), non-B (CD19), intermediate levels of CD11 c, and high levels of B220 and NK-specific markers, including NK1.1, DX5, NKG2D and Ly49 family receptors. IKDCs functionally resemble NK cells in cytotoxicity against cancer cells and in production of abundant IFN-•. On the other hand, upon stimulation with CpG or cancer cells, IKDCs down-regulate NKG2D, up-regulate MHC II, and acquire moderate APC-like activity that activates antigen-specific T cells. Despite acquisition of APC activity after certain stimulations, IKDCs appear to belong to the NK lineage rather than DC lineage. IKDCs express NK-specific Ncr-1 transcripts (encoding NKp46) but not PU.1 that is predominantly expressed in DCs and plasmacytoid DCs. Furthermore, IKDC development parallels NK cells in their strict dependence on the IL-15 cytokine system. Therefore, the putative IKDCs are functionally and developmentally similar to NK cells. Although debates regarding tumoricidal activity and cell lineage development of IKDC were raised herein, further investigations were limited by rare abundance of IKDC in periphery. The frequency of IKDCs in a mouse spleen is below 0.01%, and is even lower in the lymph nodes. Therefore, cumbersome procedure is required for the purification of IKDCs, and the yield is low. This problem has limited the use of IKDCs in research and in application.

Thus, Applicant put a lot of efforts in the past years and successfully screens out cells which have the functions of both natural killer cells and dendritic Cells. The abovementioned cells are defined as Dendritic Killer Cell (hereafter called DKC), also be called cytotoxic dendritic cell (cytoDC).

However, it is noted that the DKC constitutes less than 0.01% of peripheral lymphocytes. Please refer to FIG. 1 to FIG. 2B; FIG. 1 is a diagram showing the percentage of DKC in human peripheral blood of the cancer patient and the healthy donor. FIG. 2A is a diagram showing the result of using a flow cytometer to analyze human peripheral blood of a cancer patient in the preferred embodiment of the present invention, and FIG. 2B is a diagram showing the result of using a flow cytometer to analyze human peripheral blood of a healthy donor in the preferred embodiment of the present invention. As shown in FIG. 1, the percentage of the DKC in human peripheral blood of the cancer patient is obviously lower than that of the healthy donor. Furthermore, as shown in the upper right corner of FIG. 2A, it is noted that the percentage of the DKC 10 in the human peripheral blood of the cancer patient is only 0.0367%. However, as shown in the upper right corner of FIG. 2B, the percentage of the DKC 10 in the human peripheral blood of the healthy donor is 0.436%. That is, the counts of the DKC which are existed in the human peripheral blood of the healthy donor are higher than that of the cancer patient.

On the other hand, cancer cells will undergo mutation to avoid identifying from immune cells so that the curative effect of the immune cell therapy cannot reach an original expectation.

SUMMARY OF THE INVENTION

According to the abovementioned disadvantages of the prior art, Applicant successfully makes trace DKC of human blood increase in an amount of 200-fold to 400-fold, and further make the expanded DKC acquire antigen-presenting cell activities. A formulation will be prepared by combing the abovementioned DKC presenting specific antigens and a physiologically acceptable medium or buffer, and activates T cells to form specific T cells.

The present invention provides a formulation for preparing specific T cells, and the formulation comprises at least a cell population of dendritic killer cells presenting specific antigens.

Preferably, the formulation further comprises a physiologically acceptable medium or buffer. Preferably, the cell population of dendritic killer cells has a concentration of $10^6$ cell/mL. Preferably, the specific antigens are cancer-specific antigens.

The present invention further provides a composition containing a plurality of cancer antigen-pulsed human DKCs, wherein the plurality of cancer antigen-pulsed human DKCs is obtained by contacting a population of human DKCs with cells derived from a cancer patient, the population of human DKCs being HLA-G$^-$ CD14$^-$ CD19$^-$ CD3$^-$ CD56$^+$ HLA-DR$^+$.

The present invention further provides a method for preparing the abovementioned formulation, and the method comprises the following steps. First, a cell population of dendritic killer cells is provided. A target sample is then provided, and a step of making the cell population of dendritic killer cells co-cultivate with the target sample is performed. After co-cultivating, a cell population of dendritic killer cells presenting specific antigens is harvested.

Preferably, the cell population of dendritic killer cells processes a cytotoxic reaction against the target sample and presents the specific antigens of the target sample on the surface. The DKCs became antigen-loaded antigen-presenting cells.

Preferably, the target sample is cancer cells from a cancer patient, and the specific antigens are cancer-specific antigens. Preferably, the target sample and the cell population of dendritic killer cells are both gathered from the cancer patient.

Preferably, the cell population of the dendritic killer cell is generated ex vivo by culturing dendritic killer cells from a human blood sample with a cytokine, and the cytokine comprises IL-15.

Preferably, the method is a platform for screening specific antigens.

The present invention further provides a method for preparing specific T cells, and the method comprises the following steps. A cell population of T cells is provided at first. And then, a formulation of preparing specific T cells is added to mix with the cell population of T cells. After cultivating, the specific T cells are harvested.

Preferably, the formulation comprises a cell population of dendritic killer cells presenting specific antigens.

Preferably, the cell population of T cells is activated by the cell population of dendritic killer cells presenting specific antigens to form the specific T cells, and the specific antigens are cancer-specific antigens. Preferably, the specific T cells are cancer-specific T cells.

The present invention further provides a cancer treatment method for a human subject in need thereof, the method comprising: First, provide a plurality of cancer antigen-pulsed human DKCs that is prepared by contacting a population of human DKCs with cells derived from a cancer patient in the subject, the population of DKCs being HLA-G$^-$ CD14$^-$ CD19$^-$ CD3$^-$ CD56$^+$ HLA-DR$^+$. Then, contact a population of CD8$^+$ T-cells with the plurality of cancer antigen-pulsed human DKCs to generate cancer antigen-specific CD8$^+$ T-cells. Finally, deliver the cancer antigen-specific CD8$^+$ T-cells to the human subject.

The present invention further provides a method for preparing a composition, wherein the composition comprises $10^6$ cell/mL dendritic killer cells presenting a specific antigen, and the method comprises the following steps:
(a) obtaining human peripheral blood mononuclear cells;
(b) culturing the cells with IL-15 and 0.5~20 ng/mL IL-12;
(c) sorting the cells expressing the cell surface marker HLA-G$^-$ CD14$^-$ CD19$^-$ CD3$^-$ CD56$^+$ HLA-DR$^+$ to obtain dendritic killer cells, wherein the dendritic killer cells have cytotoxicity activity and antigen-presenting activity;
(d) co-culturing the dendritic killer cells with a plurality of target cells, wherein the target cells express a specific antigens; and
(e) obtaining the dendritic killer cells presenting the specific antigen.

The present invention further provides a method for preparing specific T cells comprising the following steps:
(a) obtaining human peripheral blood mononuclear cells;
(b) culturing the cells with IL-15 and 0.5~20 ng/mL IL-12;
(c) sorting the dendritic killer cells, wherein the dendritic killer cells are cells with the cell surface marker HLA-G$^-$ CD14$^-$ CD19$^-$ CD3$^-$ CD56$^+$ HLA-DR$^+$;
(d) co-culturing the dendritic killer cells with a plurality of target cells, wherein the target cells express a specific antigens;
(e) harvesting the dendritic killer cells presenting the specific antigen;
(f) mixing the dendritic killer cells presenting the specific antigen with a cell population of T cells and co-culturing for a period; and
(g) harvesting the specific T cells.

Preferably, in the step (d) and (e), the dendritic killer cells kill the target cells and present the specific antigens of the target cells on their surface to form the dendritic killer cells presenting the specific antigen.

Preferably, in the step (d), the target cells are cancer cells.

Preferably, in the step (d), the specific antigen is a cancer-specific antigen.

Preferably, in the step (d), the target cells and the dendritic killer cells are both obtained from a cancer patient.

Preferably, in the step (b), the concentration of IL-15 is 10 ng/mL, or the concentration of IL-12 is 2 ng/mL.

Preferably, in the step (e), the dendritic killer cells presenting the specific antigen are capable of activating specific CD8$^+$ T cells.

Preferably, the T cells in the step (f) are isolated CD8$^+$ T cells, and the specific T cells in the step (g) are specific CD8$^+$ T cells.

Preferably, in the step (f) and (g), the cell population of T cells is activated by the dendritic killer cells presenting the specific antigen to form the specific T cells.

Preferably, the target cells, the dendritic killer cells, and the cell population of T cells are obtained from a cancer patient.

Preferably, the specific T cells are cancer-specific T cells.

The present invention further provides a method of preparing a plurality of cancer antigen-specific CD8$^+$ T cells, the method comprising the following steps:
- (a') obtaining human peripheral blood mononuclear cells;
- (b') culturing the cells with IL-15 and 0.5~20 ng/mL IL-12;
- (c') sorting the dendritic killer cells, wherein the dendritic killer cells are cells with the cell surface marker HLA-G$^-$ CD14$^-$ CD19$^-$ CD3$^-$ CD56$^+$ HLA-DR$^+$;
- (d') co-culturing the dendritic killer cells with a plurality of cancer cells, wherein the cancer cells express a cancer antigen;
- (e') harvesting the dendritic killer cells presenting the cancer antigen;
- (f') contacting a population of CD8$^+$ T cells with the dendritic killer cells presenting the cancer antigen; and
- (g') harvesting a plurality of cancer antigen-specific CD8$^+$ T cells.

Preferably, the cancer cells, the dendritic killer cells, and the cell population of CD8$^+$ T cells are obtained from a cancer patient.

The present invention further provides a cancer treatment method for a human subject in need thereof, the method comprising:
- (a") obtaining human peripheral blood mononuclear cells from the human subject;
- (b") culturing the cells with IL-15 and 0.5~20 ng/mL IL-12;
- (c") sorting the dendritic killer cells, wherein the dendritic killer cells are cells with the cell surface marker HLA-G$^-$ CD14$^-$ CD19$^-$ CD3$^-$ CD56$^+$ HLA-DR$^+$;
- (d") co-culturing the dendritic killer cells with a plurality of cancer cells obtained from the human subject, wherein the cancer cells express a cancer antigen;
- (e") harvesting the dendritic killer cells presenting the cancer antigen;
- (f") contacting a population of CD8$^+$ T cells obtained from the human subject with the dendritic killer cells presenting the cancer antigen;
- (g") harvesting a plurality of cancer antigen-specific CD8$^+$ T cells; and
- (h") delivering the cancer antigen-specific CD8$^+$ T cells to the human subject.

The features and advantages of the present invention will be understood and illustrated in the following specification and FIGS. 1~12C.

DETAILED DESCRIPTION OF THE INVENTION

Figure 1:
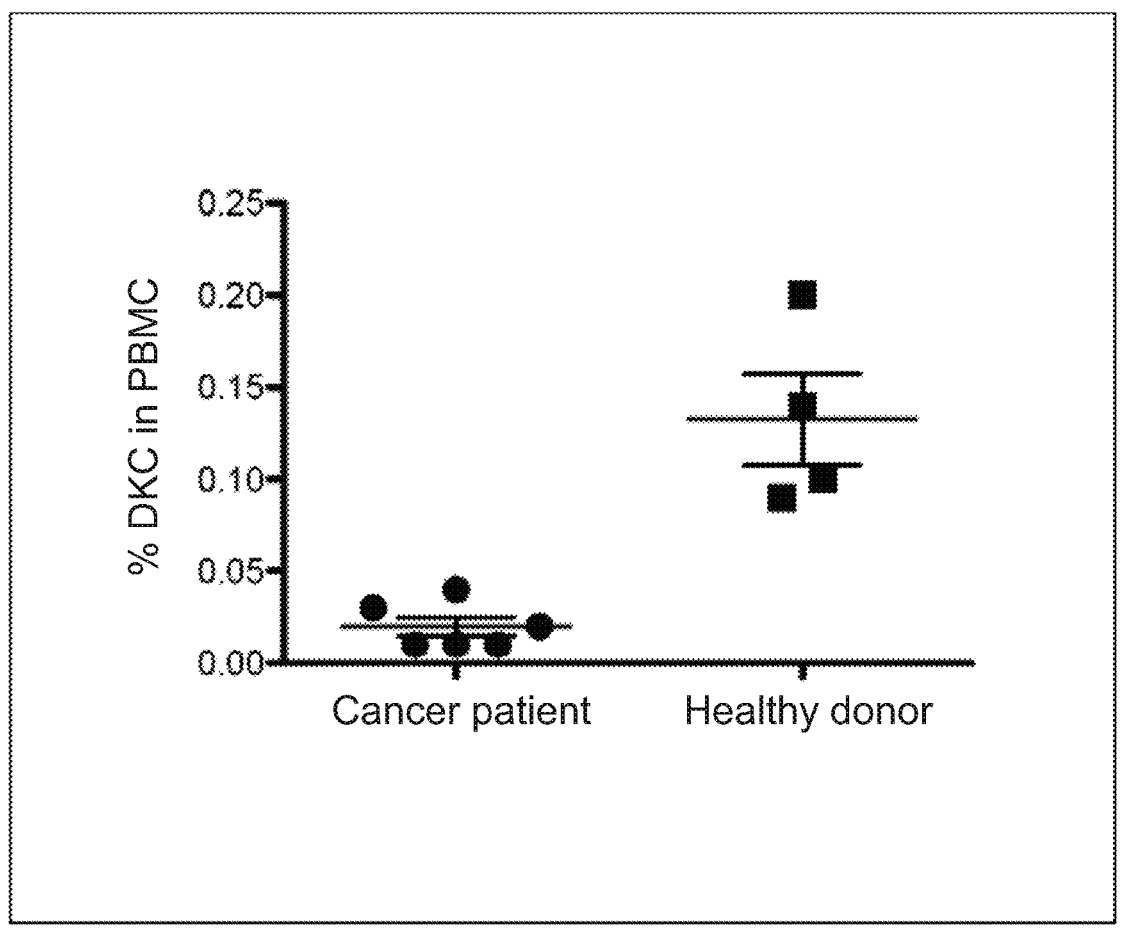
FIG. 1 is a diagram showing the percentage of DKC in human peripheral blood of the cancer patient and the healthy donor.
Figure 2A:
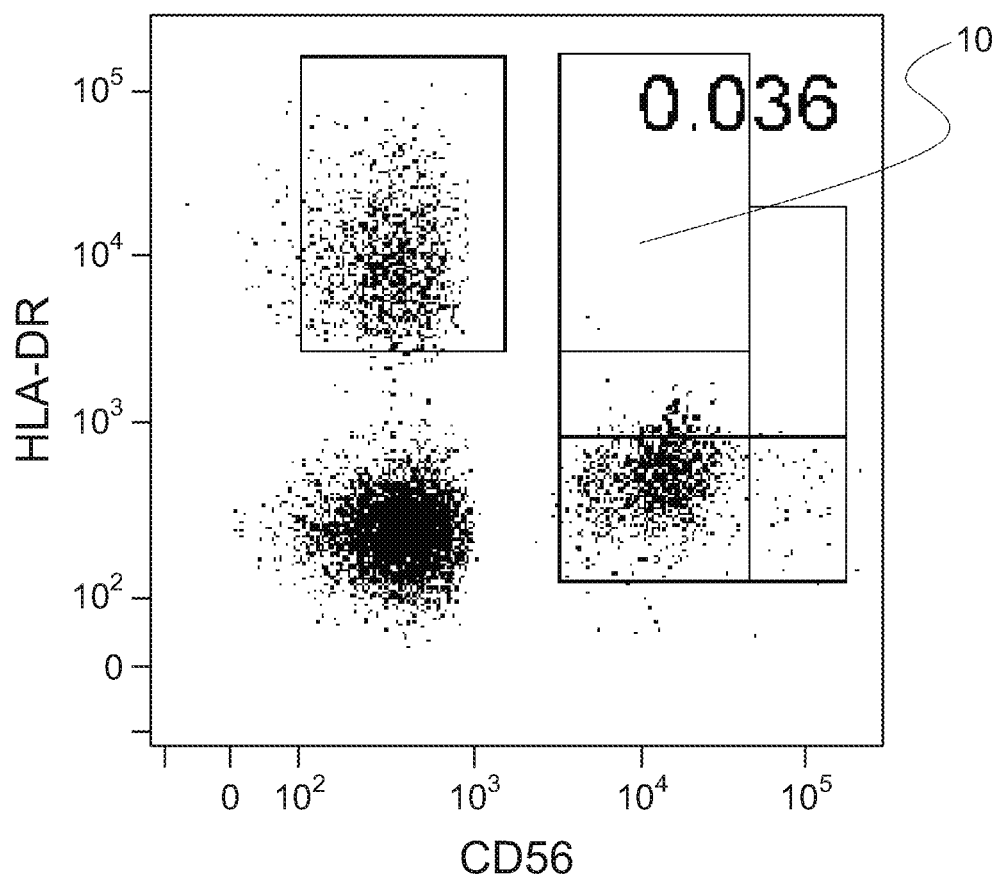
FIG. 2A is a diagram showing the result of using a flow cytometer to analyze human peripheral blood of a cancer patient in the preferred embodiment of the present invention.
Figure 2B:
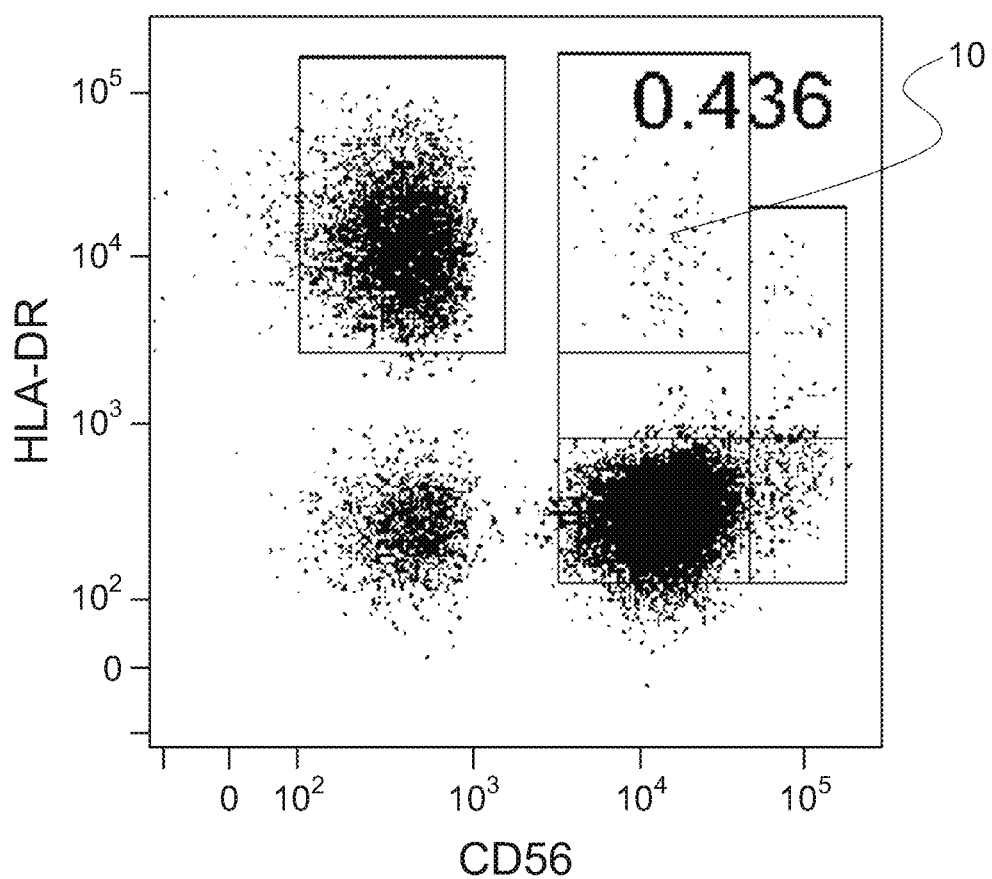
FIG. 2B is a diagram showing the result of using a flow cytometer to analyze human peripheral blood of a healthy donor in the preferred embodiment of the present invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

As used herein, the term "Dendritic killer cells" or "DKC" is intended to refer to the cells with both cytotoxicity and antigen presenting cell (APC) activity.

As used herein, the term "Dendritic killer cells presenting specific antigens" means that the surfaces of the dendritic killer cells have presented the specific antigens.

As used herein, the term "antigen-pulsed human DKC" means that the human DKC have presented the specific antigen on its surface.

As used herein, the term "specific T cells" or "antigen-specific CD8$^+$ T-cell" means that T cells activated by antigen-presenting cells are specific for the antigen presented by the above antigen-presenting cells.

As used herein, the term "cancer" (i.e. malignant tumor) is a group of diseases characterized by uncontrolled growth and spread of abnormal cells. From a histological standpoint there are hundreds of different cancers, which are grouped into six major categories: carcinoma, sarcoma, myeloma, leukemia, lymphoma, and mixed types. Many cancers form solid tumors, which are masses of tissue; cancers of the blood, such as leukemias, generally do not form solid tumors. (Please refer to the website of National Cancer Institute, http://www.cancer.gov/; http://training.seer.cancer-.gov/disease/categories/classification.html).

On the other hand, different body tissue types (e.g. connective tissue, endothelium and mesothelium, blood and lymphoid cells, muscle, epithelial tissues, and neural et al) give rise to different tumors, both benign and malignant. Different malignant tumors, containing solid malignant tumors and non-solid malignant tumor, are relevant to different cancers. (Please refer to the website of National Cancer Institute, http://training.seer.cancer.gov/disease/categories/tumors.html).

As used herein, the term "cancer cell" means a cell that is part of a malignant tumor.

As used herein, the term "cancer antigen" means a substance produced in cancer cells and capable of inducing immune response in the host.

As used herein, the term "cancer-specific antigen" means a substance produced in cancer cells and capable of inducing immune response in the host.

As used herein, the term "cancer-specific T cell" means a T cell that specific recognizes a cancer antigen and thus could be activated by the antigen-presenting cells presenting the cancer antigen.

As used herein, the term "cancer antigen-specific CD8$^+$ T cell" means a CD8$^+$ T cell that specifically recognizes a cancer antigen and thus could be activated by the antigen-presenting cells presenting the cancer antigen.

As used herein, the symbol "+" means that the cell surface marker expresses on the surfaces of the cells and has a larger expressed amount measured by flow cytometer than that of the negative control.

As used herein, the symbol "−" means that the cell surface marker does not express on the surfaces of the cells and has an expressed amount equal to that of the negative control.

Preferably, all abovementioned expressed amount of the cell surface markers are measured by flow cytometer; however, the present invention is not limited thereto.

As used herein, the term "Interleukin" means a group of cytokines that were first seen to be expressed by white blood cells (leukocytes). It has since been found that interleukins are produced by a wide variety of body cells. The function of the immune system depends in a large part on interleukins.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention. To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Preferably, several sorting or screening steps are performed by a flow cytometer, and a target cell population will be screened out by utilizing at least one flow cytometer to identify different surface markers of different cells. Flow cytometry allows for single cell analysis at speeds far surpassing any other single cell analysis technology in the art. This enables a statistically significant number of cells to be analyzed faster than using other alternative techniques. In a preferred embodiment, a flow cytometer is used with any suitable sample preparation robot or liquid handler that is known in the art. Furthermore, a single laser flow cytometer is used in an embodiment for the analyzing step. In another embodiment, a multi-laser flow cytometer is used for the analyzing step and the present invention is not limited thereto.

At first Applicant put a lot of efforts in the past years and successfully screens out cells which have the functions of both natural killer cells and dendritic Cells. These cells are defined as dendritic killer cell (hereafter called DKC) as mentioned above and have surface markers of HLA-G$^-$ CD14$^-$ CD19$^-$ CD3$^-$ CD56$^+$ HLA-DR$^+$.

Prepare Dendritic Killer Cells

Figure 3:
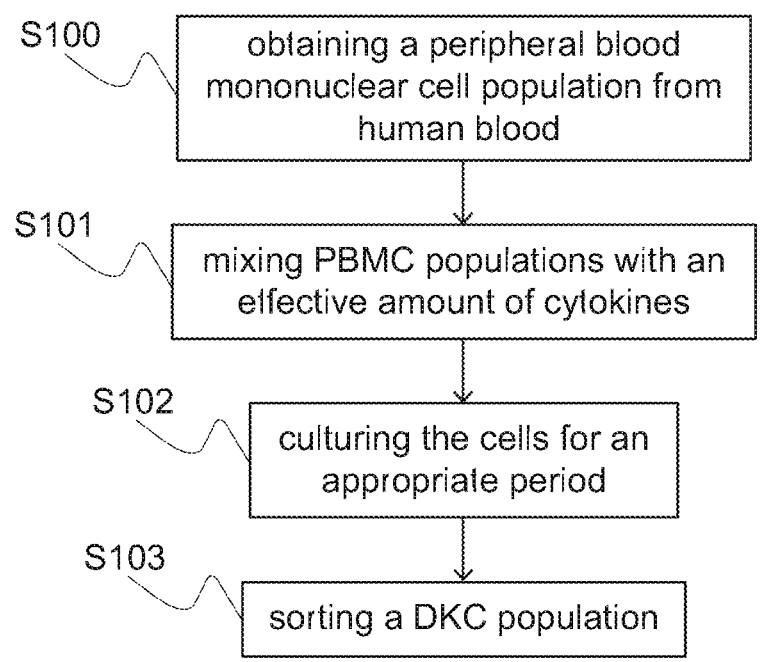
FIG. 3 is a flow chart showing a method according to an embodiment of the present invention for cultivating DKC population.

As abovementioned, the DKCs are identified from human peripheral blood. Please refer to FIG. 3; FIG. 3 is a flow chart showing a method for cultivating DKC population. First, step S100 of obtaining a peripheral blood mononuclear cell population from human blood is performed. And then, step S101 of adding an effective amount of at least a cytokine to mix with the peripheral blood mononuclear cell population is performed. Preferably, the cytokine comprises an effective amount of Interleukin-15 (hereafter "IL-15"). The following step S102 is to place the peripheral blood mononuclear cell population for an appropriate period. Finally, a DKC population will be sorted in step S103.

Preferably, the abovementioned cytokine in step S101 further comprises Interleukin-12 (hereafter "IL-12"). Preferably, the concentration of abovementioned IL-15 is 10 ng/mL, and the concentration of IL-12 is a value between 0.5~20 ng/mL.

Preferably, the abovementioned step S100 further comprises the following steps. At first, the 40 ml peripheral blood is gathered and the human peripheral blood mononuclear cell (hereafter "PBMC") is sorted. T cells and B cells are then removed from the peripheral blood mononuclear cell population. Finally, the concentration of the peripheral blood mononuclear cell population will be adjusted to $10^6$ cell/mL. The human peripheral blood mononuclear cells comprise the following five categories of cells: monocytic cells, small cells, lymphoid cells, large cells and large and granular cells. Flow cytometry can be first used to select one or more types of cells for follow steps. The cell preferably comprises monocytic cells or lymphoid cells or both, and the monocytic cell population will be used as a preferred embodiment in the following. However, the present invention is not limited thereto.

Preferably, the abovementioned appropriate period means that IL-15 and the peripheral blood mononuclear cell population are both put into a media for a period to let cell proliferation process. Preferably, the appropriate period is the seventh day after starting the abovementioned cultivating step.

Example

In step S100', obtain 40 mL blood form an ovarian cancer patient. Isolate peripheral blood mononuclear cell population from the blood, and then remove B cells (CD19$^+$) and T cells (CD3$^+$) from the peripheral blood mononuclear cell population to obtain peripheral blood mononuclear cell population without CD3$^+$ cells and CD19$^+$ cells therein.

In step S101', mix these remained peripheral blood mononuclear cells (CD3⁻ CD19⁻) with 10 ng/mL IL-15 and 2 ng/mL IL-12.

In step S102', culture for 7 days.

In step S103', use flow cytometry to sort the cells expressing the cell surface marker HLA-G⁻ CD14⁻ CD19⁻ CD3⁻ CD56⁺ HLA-DR⁺. These sorted HLA-G⁻ CD14⁻ CD19⁻ CD3⁻ CD56⁺ HLA-DR⁺ cells are the dendritic killer cells of the present invention.

Figure 4A:
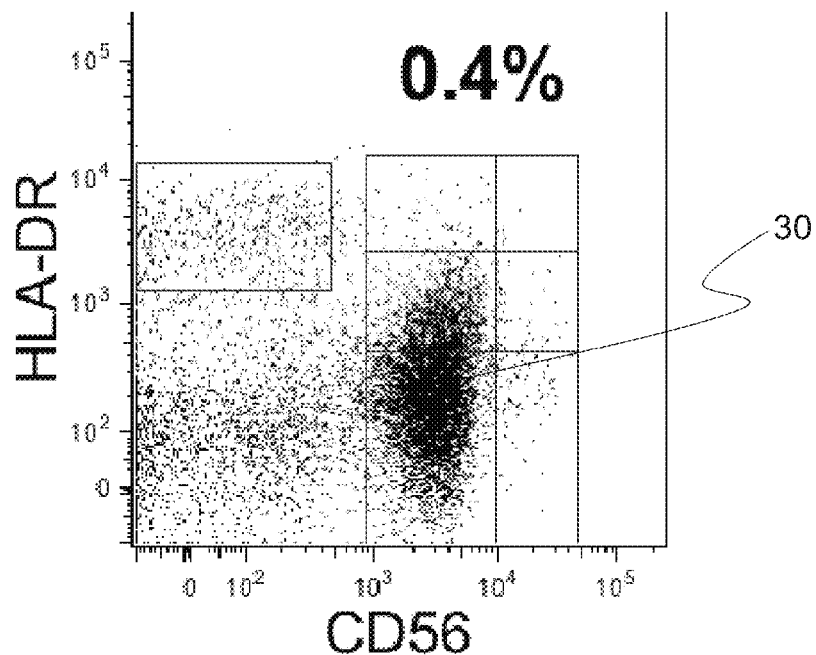
FIG. 4A to FIG. 4C are diagrams showing the results of detecting and screening cultivated DKC population by a flow cytometer.
Figure 4B:
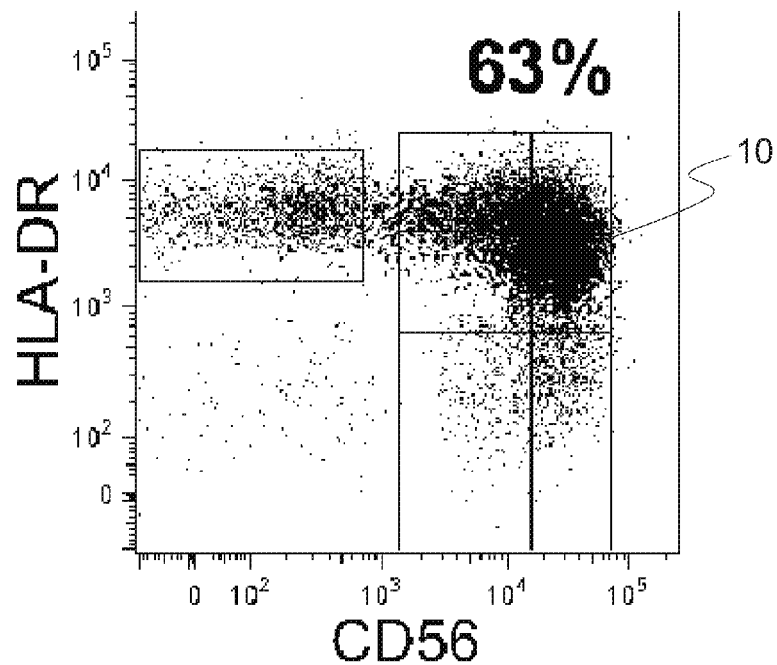
Figure 4C:
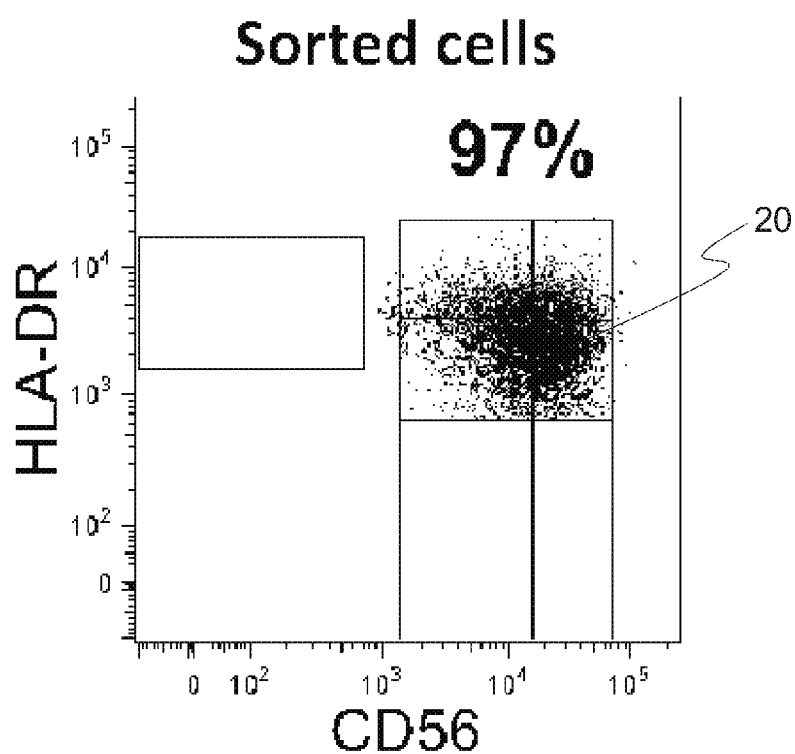

Result:

Please refer to FIG. 4A to FIG. 4C; FIG. 4A to FIG. 4C are diagrams showing the results of detecting and screening cultivated DKC population by a flow cytometer. First, FIG. 4A illustrates the results of detecting the surface markers of CD56 and HLA-DR by a flow cytometer after removing the T cell and B cell (CD3⁻ CD19⁻ PBMC) from human peripheral blood mononuclear cells and before cultivating (cells obtained from step S100'). FIG. 4B illustrates the results of detecting the surface markers of CD56 and HLA-DR by a flow cytometer at the seventh day after starting the cultivating step (cells obtained from step S102'). FIG. 4C illustrates the results of sorting DKC population by a flow cytometer (cells obtained from step S103').

As shown in FIG. 4A, the counts of the cells which have natural killer cell surface marker (CD56⁺) and dendritic Cell surface marker (HLA-DR⁺) are much fewer; the proportion of this population is about 0.4%. And further, the cells 30 positioned at the central portion are natural killer cells which have the surface marker of CD 56 but not HLA-DR. Please refer to FIG. 4B, after culture with 10 ng/mL IL-15 and 2 ng/mL IL-12 for 7 days, the cells will transfer to the DKC 10 which has both natural killer cell surface marker (CD56⁺) and dendritic cell surface marker (HLA-DR⁺); the proportion of this DKC 10 population is about 63%. The DKCs expand the counts and further let natural killer cells transfer to DKC. Finally, FIG. 4C illustrates the sorted cells selected by flow cytometer, the DKC population 20 which has the surface marker of HLA-G⁻ CD14⁻ CD19⁻ CD3⁻ CD56⁺ HLA-DR⁺.

It is noted that the abovementioned appropriate period is the preferred embodiment; however, the present invention is not limited thereto. That is, the step S103 can be performed on the fourth day after cultivating or on the tenth day after cultivating. Or, in the step S102, the cells can be cultured for 4~10 days, or the cells can be cultured for several days. Furthermore, the steps S101~S103 can be repeatedly performed after the step S103. That is, non-adherent cells will be collected again and the counts of the dendritic killer cells will be expanded to an expect value by repeating the abovementioned steps.

Preferably, the method disclosed in the present invention is processed ex vivo, wherein the human blood is collected from a cancer patient. And further, a cancer, which the cancer patient suffers from, can be selected from a group consisting of squamous cell carcinoma, lobular carcinoma in situ, liver cancer, nasopharyngeal carcinoma, lung cancer, bone cancer, pancreatic cancer, skin cancer, head and neck cancers, malignant melanoma, cervical cancer, ovarian cancer, colon cancer, anal cancer, stomach cancer, breast cancer, testicular cancer, fallopian tube cancer, endometrial cancer, cervical cancer, vaginal cancer, vulvar cancer, non-Hodgkin lymphoma, Hodgkin lymphoma, esophageal cancer, thyroid cancer, adrenal cancer, cancers of mesothelial and soft tissue, urethra cancer, cancer of penis, prostate cancer, acute leukemia, chronic leukemia, lymphomas, bladder cancer, ureteral cancer, renal cell carcinoma, urothelial carcinoma, cancer of central nervous system, primary central nervous system lymphoma, glioma, pituitary tumor, Kaposi's sarcoma, squamous cell cancer and their metastasis.

In the following, the present invention provides a formulation for preparing specific T cells, and the formulation comprises at least a cell population of dendritic killer cells presenting specific antigens. Furthermore, the formulation comprises a physiologically acceptable medium or a physiologically acceptable buffer. It is noted that the cell population of the dendritic killer cells presenting specific antigens is obtained by further dealing with the abovementioned cultivated DKC population, and the cell population of the dendritic killer cells has absolutely different characteristics from the DKC population.

It is needed to be further illustrated that the cell population of the dendritic killer cells included within the formulation is a cell population of dendritic killer cells presenting specific antigens. And further, the formulation is used to induce specific T cell responses. That is to say, the present invention also discloses a method for preparing specific T cells by utilizing the abovementioned cell population of the dendritic killer cells presenting specific antigens. The above formulation and method for preparing specific T cells, and method for preparing the formulation are both illustrated with figures as the following.

Figure 5:
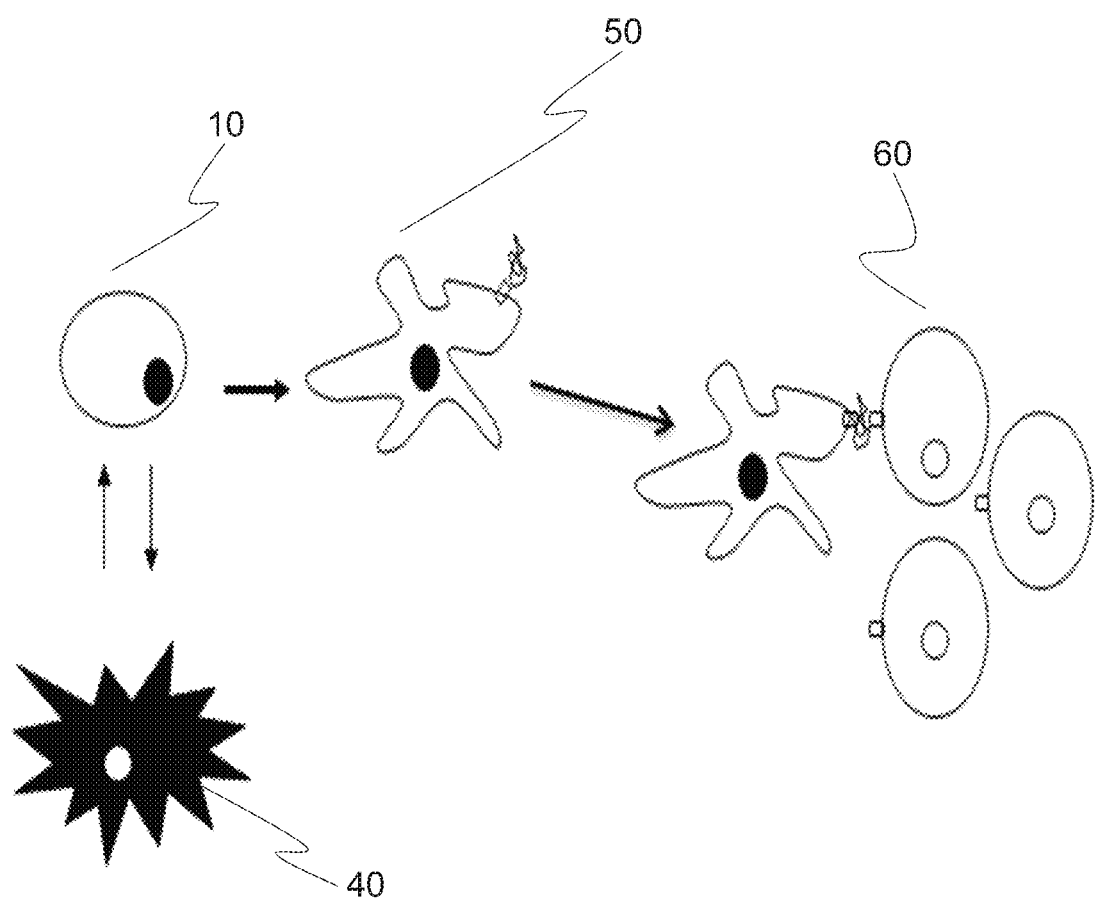
FIG. 5 is a diagram showing an operational mechanism of DKC.

Please refer to FIG. 5; FIG. 5 is a diagram showing an operational mechanism of DKC. As shown in the figure, the dendritic killer cells 10 can identify cancer cells 40. After identifying, the dendritic killer cells 10 will produce interferon-γ (hereafter "IFN-γ") to kill the cancer cells 40 by their cytotoxicity and further swallow the fragments of the killed cancer cells 40 to present cancer-specific antigens on their surface and therefore become the cell population of the dendritic killer cells presenting specific antigens 50. The above cell population of the dendritic killer cells presenting specific antigens 50 will present the cancer-specific antigens to CD8⁺ T cells 60 to activate CD8⁺ T cells. After activating, the CD8⁺ T cells become specific T cells.

Prepare Dendritic Killer Cells Presenting Specific Antigens

Figure 6:
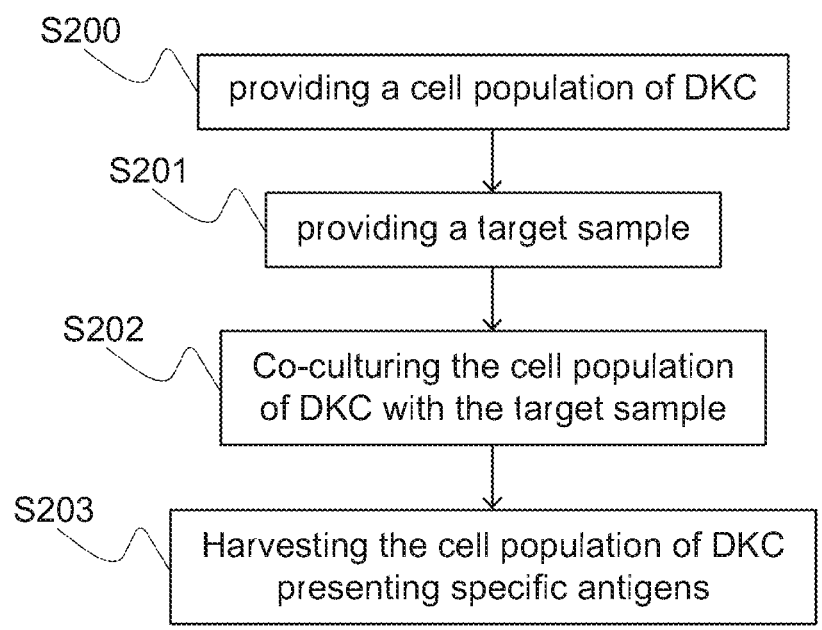
FIG. 6 is a flow chart showing a method according to an embodiment of the present invention for fabricating a formulation of preparing specific T cells.
Figure 7A:
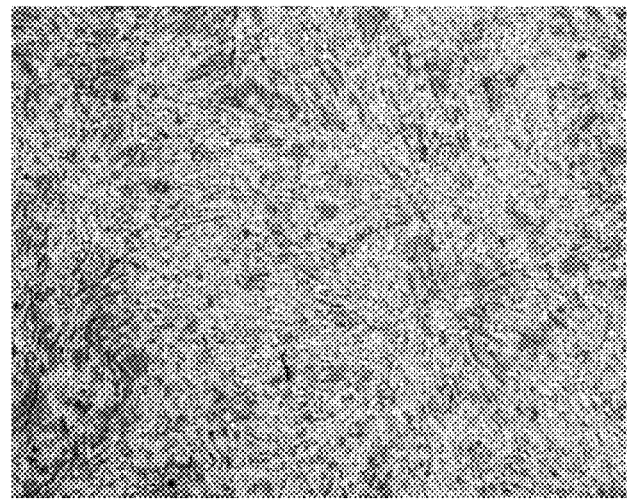
FIG. 7A to FIG. 7B are diagrams showing different conditions of ovarian cancer cells before and after adding DKC population therein.
Figure 7B:
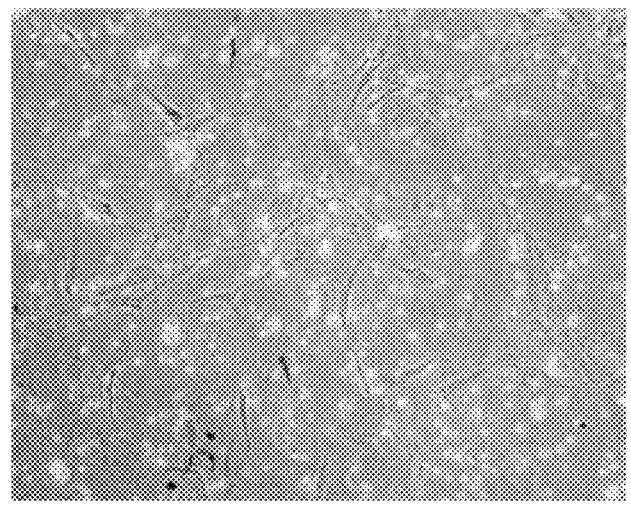

Please refer to FIG. 6, FIG. 7A and FIG. 7B. FIG. 6 is a flow chart showing a method according to an embodiment of the present invention for preparing a formulation of preparing specific T cells, and FIG. 7A to FIG. 7B are diagrams showing different conditions of ovarian cancer cells before and after adding DKC population therein.

As shown in FIG. 6, the cultivated cell population of the dendritic killer cells is obtained in the step S103, and the cultivated cell population of the dendritic killer cells can be further used in the following method for preparing the above formulation in step S200. A target sample is then provided in step S201. Preferably, the target sample is the cancer cell gathered from the same cancer patient. For example, the target sample is ovarian cancer cells of the abovementioned cancer patient and the ovarian cancer cells obtained from patient surgery were then put into a medium.

Example

In step S200', obtain the cell population of dendritic killer cells which comes from the step S103'.

In step S201', obtain the ovarian cancer cells from the ovarian cancer patient who is the same one as in the step S100'. The ovarian cancer cells will be used as a target sample.

In step S202', Co-culture the cell population of dendritic killer cells with the ovarian cancer cells (target sample).

In step S203', harvest the cell population of dendritic killer cells presenting specific antigens.

Result:

As shown in FIG. 7A, the ovarian cancer cells grew normally before react with the cell population of the dendritic killer cells. And then, a step S202 of making the cell population of the dendritic killer cells co-cultivate with the target sample is performed. The abovementioned cell population of the dendritic killer cells will show its cytotoxicity by killing the cancer cells, a lot of the cancer cells then decreases as shown in FIG. 7B. Furthermore, the cell population of the dendritic killer cells will swallow the fragments of the cancer cells to present cancer-specific antigens of the above target sample. That is, the above cell population of the dendritic killer cells will become the cancer-specific cell population of dendritic killer cells. Finally, the cancer-specific cell population of dendritic killer cells is harvested in step S203 as the formulation disclosed in the present invention. Preferably, the cell population of dendritic killer cells presenting specific antigens used in the formulation has a concentration of $10^6$ cell/mL.

Prepare Specific T Cells

Figure 8:
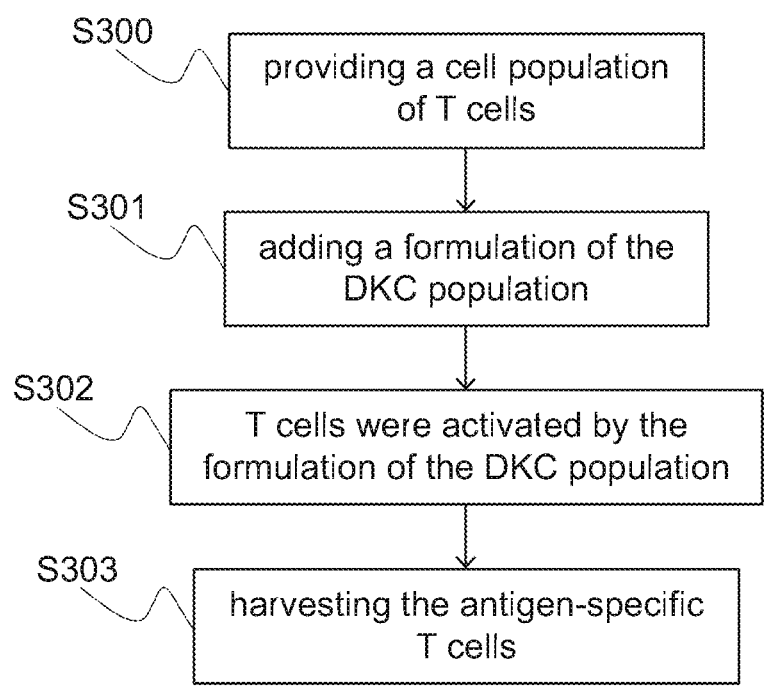
FIG. 8 is a flow chart showing a method according to an embodiment of the present invention for preparing specific T cells.

Please refer to FIG. 8; FIG. 8 is a flow chart showing a method according to an embodiment of the present invention for preparing specific T cells. The method comprises the following steps. As shown in step S300, a cell population of T cells is provided at first. And then, a formulation of preparing specific T cells is added to mix with the cell population of T cells in step S301. The cell population of the dendritic killer cells used in the formulation will present its cancer-specific antigens to activate T cells in step S302. In the step S302, the activated T cells identify the cancer-specific antigens so that those T cells become the cancer-specific T cells. Finally, the specific T cells are harvested in Step S303. Preferably, the formulation has a concentration of $10^6$ cell/mL, but the present invention is not limited thereto.

Example

In step S300', obtain the CD8$^+$ T cells from the peripheral blood of the ovarian cancer patient who is the same one as in the step S100'.

In step S301', mix the dendritic killer cells presenting the specific antigen obtained from the step S203' with the CD8$^+$ T cells.

In step S302', co-culture the cells for 48 hours.

In step S303', harvest the antigen-specific T cells.

Figure 9A:
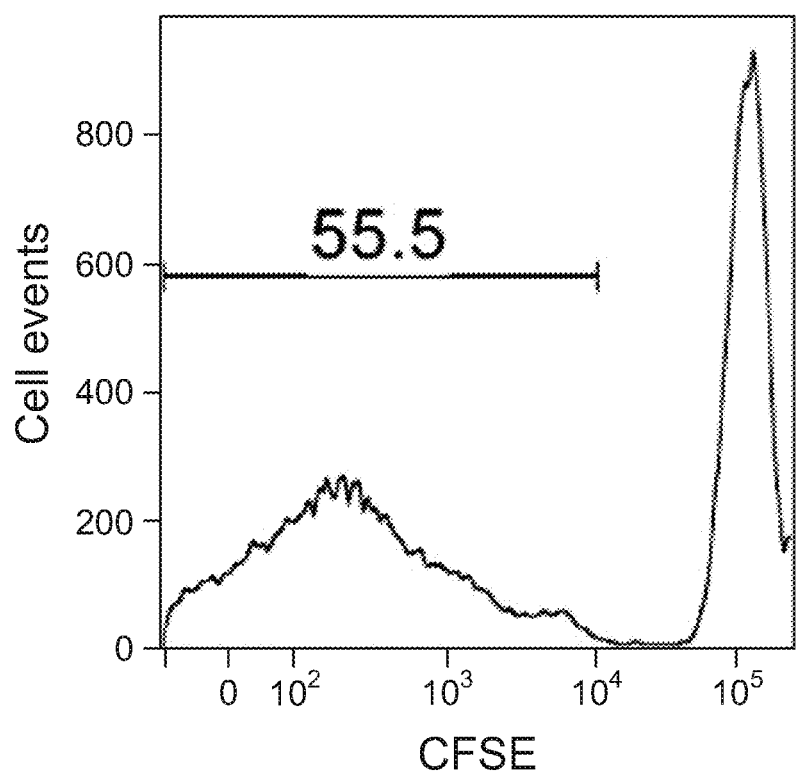
FIG. 9A and FIG. 9B are diagrams showing the result of activating T cells by the cell population of the dendritic killer cells presenting specific antigens according to an embodiment of the present invention.
Figure 9B:
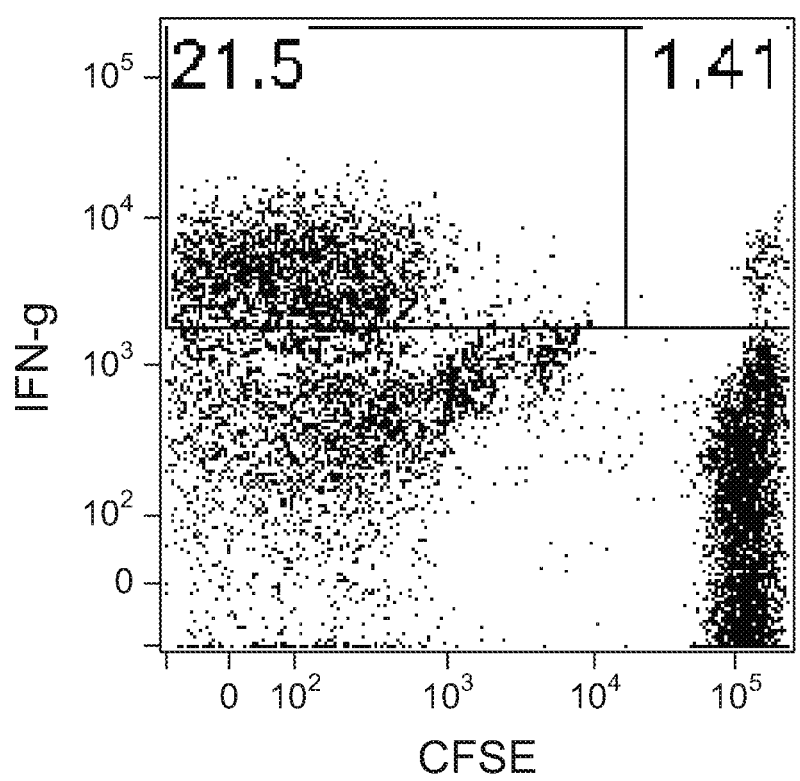
Figure 10A:
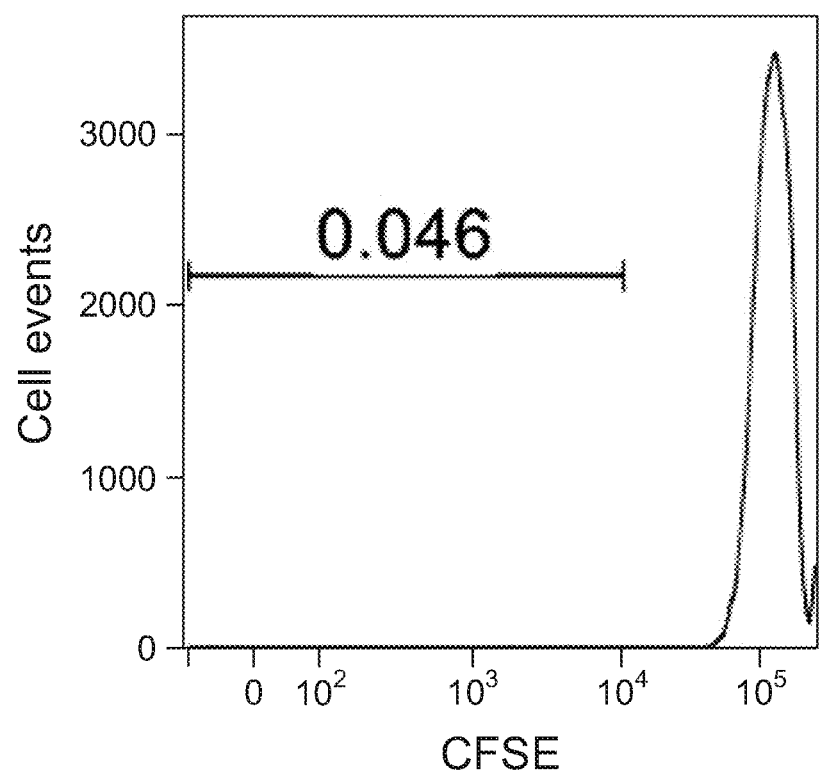
FIG. 10A and FIG. 10B are diagrams showing the result of activating T cells by the cell population of the dendritic killer cells without reacting with the cancer cells.
Figure 10B:
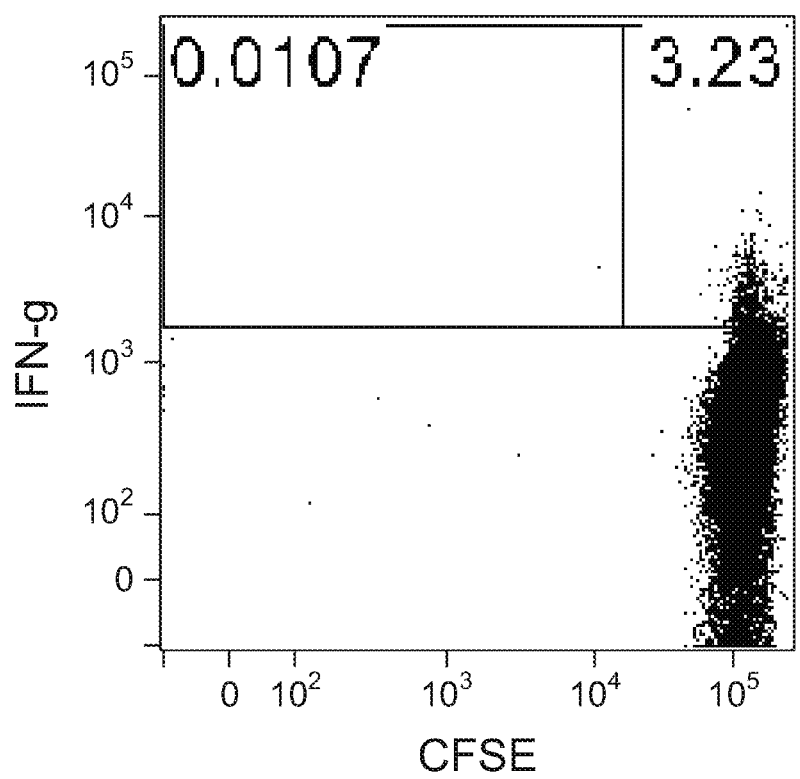

Result:

Please refer to FIG. 9A~FIG. 10B. FIG. 9A and FIG. 9B are diagrams showing the result of activating T cells by the cell population of the dendritic killer cells presenting specific antigens according to an embodiment of the present invention; FIG. 10A and FIG. 10B are diagrams showing the result of activating T cells by the cell population of the dendritic killer cells without reacting with the cancer cells. As the abovementioned, the cell population of the dendritic killer cells presenting specific antigens can activate the T cells. Therefore, CD8$^+$ T cells are sorted from the peripheral blood of the cancer patient, who is suffered from the ovarian cancer, and the sorted T cells are further marked by 6.5 μM of CFSE for observing the effect of activation of T cells. The abovementioned CFSE is a dye for quantifying the degree of cell proliferation. After each cell proliferation, the fluorescence intensity of CFSE will decrease. However, when CFSE labeling is performed optimally, approximately 7-8 cell divisions can be identified before the CFSE fluorescence is too low to be distinguished above the autofluorescence background. The present embodiment is detected by the flow cytometer, but it is not limited thereto. It is noted that the cell population of the dendritic killer cells, the cell population of the dendritic killer cells presenting specific antigens, the cancer cells and CD8$^+$ T cells are both gathered from the same cancer patient.

As shown in FIG. 9A to FIG. 9B, FIG. 9A shows the result detected by the flow cytometer for observing the cleavage of the T cells after activating, and FIG. 9B shows the result of detecting IFN-γ existed in the T cells by the flow cytometer. That is, the present invention makes the cell population of the dendritic killer cells presenting specific antigens co-cultivate with the CD8+ T cells for 48 hours and further observes the cleavage of the T cells by the flow cytometer.

Please refer to FIG. 9A; the cell population of the dendritic killer cells presenting specific antigens can activate T cells to let 55% of them proliferate. On the other hand, the T cells activated by the cell population of the dendritic killer cells presenting specific antigens have IFN-γ therein as shown in the upper-left of FIG. 9B. That is to say, the activated T cells are specific for the antigens presented by the cell population of the dendritic killer cells so that they will produce IFN-γ and have cytotoxicity.

Please refer to FIG. 10A; it is clearly that only 0.046% of T cells are proliferated. That is, the cell population of dendritic killer cells, which is not reacted with the cancer cells, cannot activate the T cells. Furthermore, there is no IFN-γ detected within the T cells as shown in FIG. 10B. Therefore, the cell population of the dendritic killer cells, which is not reacted with the cancer cells, does not present specific antigens on its surface so that it cannot activate auto CD8$^+$ T cells.

The Effect of IL-15 and IL-12 on Dendritic Killer Cells Preparation

Experiment:

In Step 1, obtain human peripheral blood mononuclear cells (PBMC) from healthy individual, and then remove B cells and T cells from the peripheral blood mononuclear cell population to obtain peripheral blood mononuclear cell population without any CD3$^+$ cells or CD19$^+$ cells therein. The CD3$^-$ CD19$^-$ PBMC are divided into three groups: "Fresh cell" group, "IL15" group, and "IL15+IL12" group.

In step 2, use flow cytometry to analysis the cell populations of "Fresh cell" group.

In step 3, seed 1×10$^6$/ml__CD3$^-$ CD19$^-$ human peripheral blood mononuclear cells in a plate and then culture the cells with 20 ng/ml (Preferably, 10~40 ng/ml) IL-15 for 10 (Preferably, 7~10) days ("IL15" group). Seed 1×10$^6$/ml CD3$^-$ CD19$^-$ human peripheral blood mononuclear cells in another plate and then culture the cells with 20 ng/ml (Preferably, 10~40 ng/ml) IL-15 and 4 ng/ml (Preferably, 0.5~20 ng/ml) IL-12 for 10 (Preferably, 7~10) days ("IL15+IL12" group).

In step 4, calculate the cell number in "IL15" group and "IL15+IL12" group. Use flow cytometry to analysis the cell populations of "IL15" group and "IL15+IL12" group.

Result:

There are only 3.15×10$^7$ cells in the "IL15" group after culturing; there are 5×10$^7$ cells in the "IL15+IL12" group after culturing.

Figure 11A:
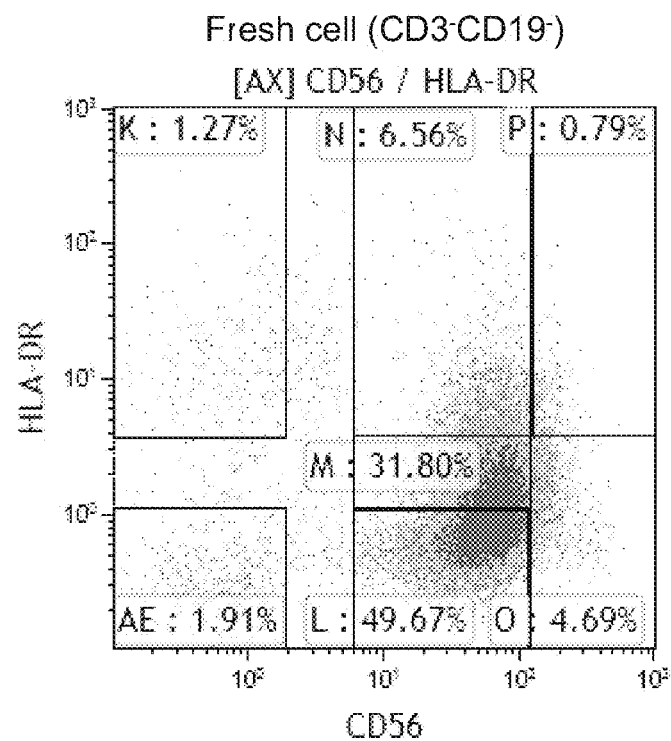
FIGS. 11A, 11B, and 11C are diagrams showing the cell populations of "Fresh cell" group, "IL15" group, and "IL15+IL12" group respectively.
Figure 11B:
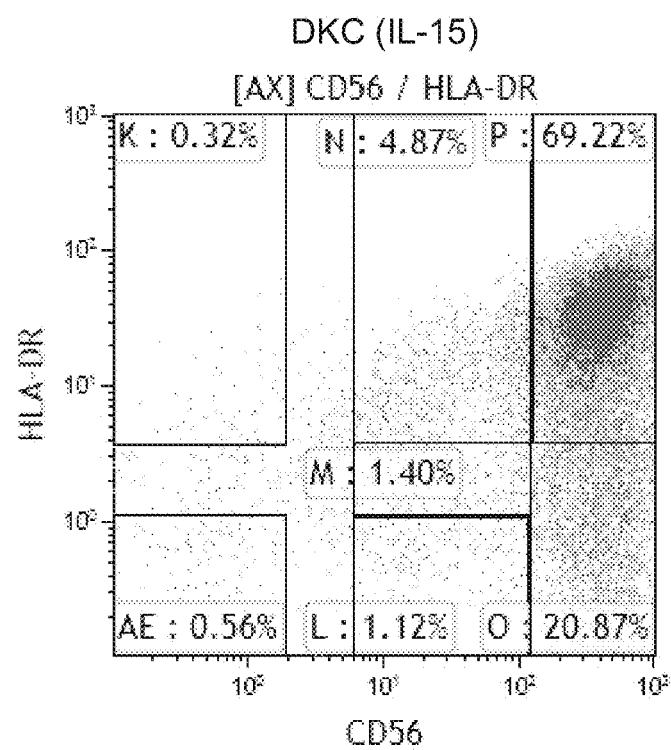
Figure 11C:
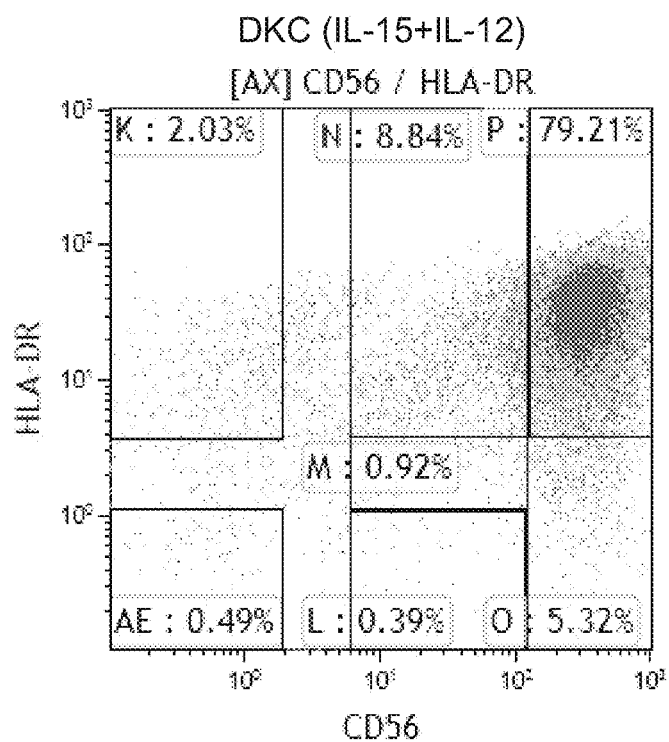

Please Refer to FIG. 11A to 11C. FIG. 11A shows the cell populations of "Fresh cell" group; FIG. 11B shows the cell populations of "IL15" group; FIG. 11C shows the cell populations of "IL15+IL12" group. In the Fresh cell group (FIG. 11A), the proportion of the cells with natural killer cell surface marker (CD56$^+$) and dendritic Cell surface marker (HLA-DR$^+$) is 0.79%. After culture with IL-15 (FIG. 11B), the proportion of the cells with natural killer cell surface marker (CD56$^+$) and dendritic Cell surface marker (HLA-DR$^+$) is much higher and becomes 69.22%. On the other hand, after culture with IL-15 and IL-12 (FIG. 11C), the proportion of the cells with natural killer cell surface marker (CD56$^+$) and dendritic Cell surface marker (HLA-DR$^+$) is even higher and becomes 79.21%. Therefore, comparing to the result shown in IL-15 group, the combination of IL-12 and IL-15 enhances the number of dendritic killer cells by 82%. [(5×10$^7$×79.21%−3.15×10$^7$×69.22%)/(3.15×10$^7$×69.22%)=82%]

The Effect of IL-15 and IL-12 on the Antigen-presenting Activity of Dendritic Killer Cells Experiment:
- In step 5 (after above-mentioned step 4), by using flow cytometry, sort the cells expressing the cell surface marker HLA-G$^-$ CD14$^-$ CD19$^-$ CD3$^-$ CD56$^+$ HLA-DR$^+$ from "IL15" group, and "IL15+IL12" group respectively to obtain dendritic killer cells therein.
- In step 6, prepare the CFSE-labeled PBMC (i.e., CFSE-labeled responder PBMC, or refer to "responder cells") from another healthy individual.
- In step 7, culture CFSE-labeled responder PBMC (hereafter called "Responder cell alone" group). In addition, co-culture dendritic killer cells obtained from the "IL15" group with CFSE-labeled responder PBMC following the ratio of two to one (hereafter called "IL15 cultured DKC and responder cell" group). On the other hand, co-culture dendritic killer cells obtained from the "IL15+IL12" group with CFSE-labeled responder PBMC following the ratio of two to one (hereafter called "IL15+IL12 cultured DKC and responder cell" group).
- In step 8, co-culture the cells for 72 hours.
- In step 9, harvest total cell from "Responder cell alone" group, "IL15 cultured DKC and responder cell" group, and "IL15+IL12" group respectively.
- In step 10, analyze CFSE-labeled responder PBMC in the three groups which process cell proliferation respectively via flow cytometry.

Figure 12A:
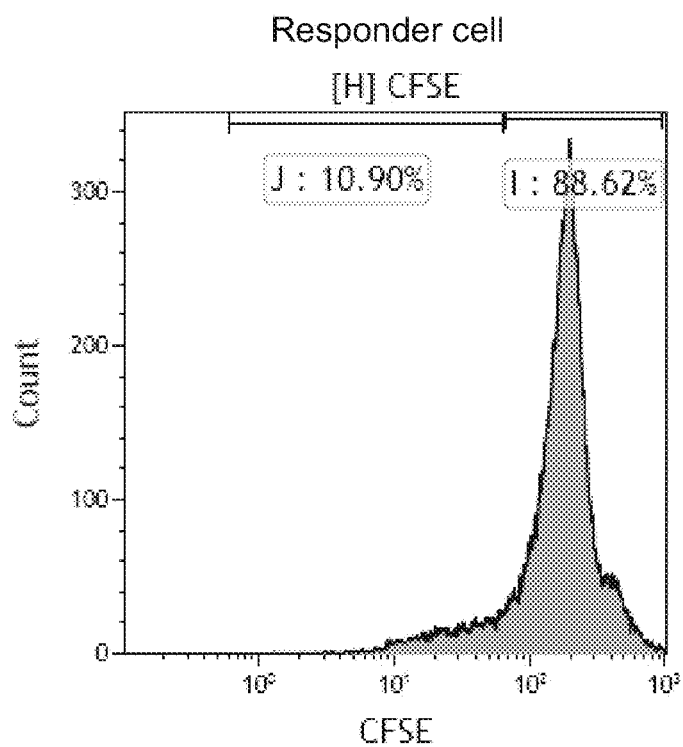
FIGS. 12A, 12B, and 12C are diagrams showing the antigen-presenting activity of dendritic killer cells in "Responder cell alone" group, "IL15 cultured DKC and responder cell" group, and "IL15+IL12 cultured DKC and responder cell" group respectively.
Figure 12B:
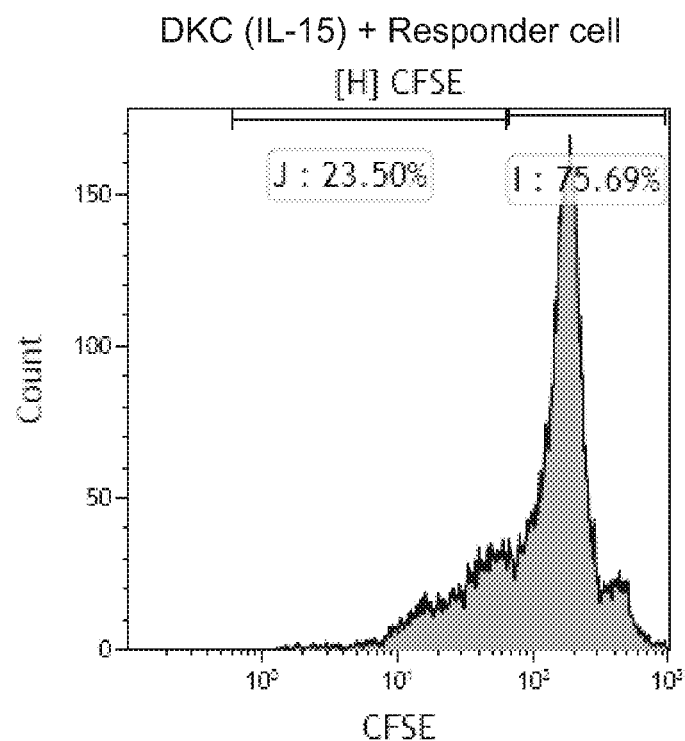
Figure 12C:
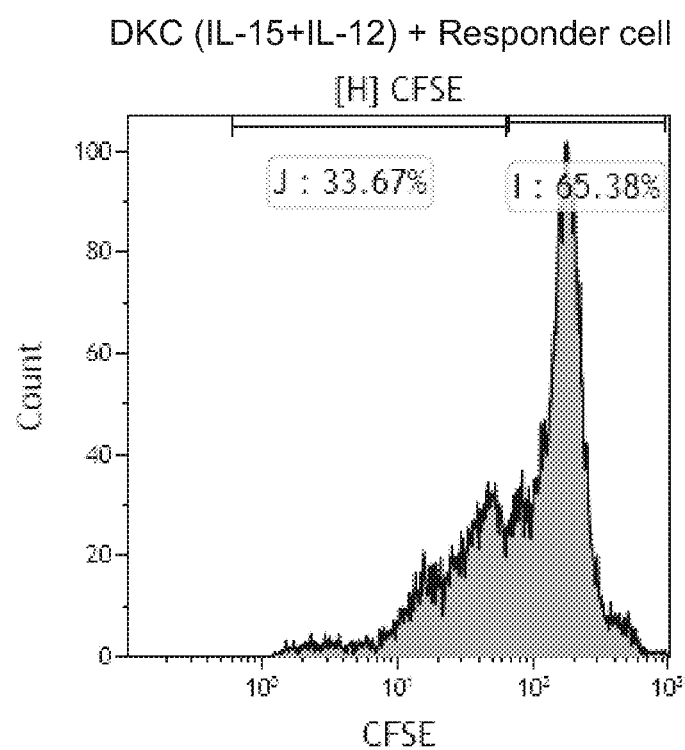

Result:

Please Refer to FIG. 12A to 12C. FIG. 12A shows the antigen-presenting activity of dendritic killer cells from "Responder cell alone" group; FIG. 12B shows the antigen-presenting activity of dendritic killer cells from "IL15 cultured DKC and responder cell" group; FIG. 12C shows the antigen-presenting activity of dendritic killer cells from the "IL15+IL12 cultured DKC and responder cell" group. Responder cells expressed 10.9% of proliferative responses in the group of "Responder cell alone". On the other hand, dendritic killer cells from the "IL15" group activates responder cells to proliferate by 23.50%. Dendritic killer cells from the IL15+IL12 group activates responder cells to proliferate by 33.67%. Therefore, comparing to the result shown in Responder cell alone, IL-15 enhances the antigen-presenting activity of DKC by 116%. [(23.5−10.9)/10.9=116%]. Besides, comparing to the result shown in IL-15 group, the combination of IL-12 and IL-15 enhances the antigen-presenting activity of DKC by 43%. [(33.67−23.5)/23.5=43%].

In this embodiment, that IL-15+IL12 cultured DKC has higher antigen-presenting activity and is capable of activating more allogeneic CD8$^+$ T cells have been proven. This information and the related mechanism indicate that after the IL-15+IL12 cultured DKCs present a cancer antigen, these DKCs presenting the specific cancer antigen will activate more autologous cancer antigen-specific CD8$^+$ T cells.

To sum up, DKC is a cell population carrying both functions of natural killer cell and dendritic cell. Although DKC plays an important role in immunoreactions, the content of the DKC in the human body is very rare. The trace DKC of the human blood can be expanded from 200-fold to 400-fold by the cultivating, screening and sorting technique disclosed in the present invention. Moreover, the DKC can kill the cancer cells by its ability of identifying cancer cells and further present the cancer-specific antigens to T cells; therefore, the cancer cells cannot avoid the identification of the immune cells. In the meantime, the target sample is gathered from the same cancer patient. That is, the cell population of the dendritic killer cells cultivated from a cancer patient will be reacted with the cancer cells obtained from the same cancer patient. After cultivating, the cell population of the dendritic killer cells presenting specific antigens will further activate CD8$^+$ T cells of the same cancer patient to form the cancer-specific T cells.

According to the abovementioned, it can be proved that the cancer cells would be recognized and killed by antigen-specific T cells, which was revealed by the method disclosed in the present invention. Furthermore, the efficiency of applying the cell population of the dendritic killer cells presenting specific antigens on preparing specific T cells has been further enhanced. Through contact a population of CD8$^+$ T cells with the plurality of cancer antigen-pulsed human DKCs, we can obtain cancer antigen-specific CD8$^+$ T cells. And administer the cancer antigen-specific CD8$^+$ T-cells to the human subject to treat cancer by their own immune cells. That is, the specific T cells prepared ex vivo can be used as a novel method of immunization therapy. On the other hand, the method disclosed in the present invention is a platform for screening the specific antigens.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

What is claim is:

1. A method for preparing antigen specific T cells comprising the following steps:
   (a) obtaining human peripheral blood mononuclear cells;
   (b) culturing the cells with IL-15 and 0.5-20 ng/mL IL-12;
   (c) sorting dendritic killer cells, wherein the dendritic killer cells are cells with the cell surface marker HLA-G$^-$CD14$^-$CD19$^-$CD3$^-$CD56$^+$HLA-DR$^+$;
   (d) co-culturing the dendritic killer cells with a plurality of target cells, wherein the target cells express a specific antigen;
   (e) harvesting the dendritic killer cells presenting the specific antigen;
   (f) mixing the dendritic killer cells presenting the specific antigen with a cell population of T cells and co-culturing for a period; and
   (g) harvesting the antigen specific T cells.

2. The method according to claim 1, wherein in the step (d) and (e), the dendritic killer cells kill the target cells and present the specific antigen of the target cells on their surface to form the dendritic killer cells presenting the specific antigen.

3. The method according to claim 1, wherein in the step (d), the target cells are cancer cells.

4. The method according to claim 3, wherein in the step (d), the specific antigen is a cancer-specific antigen.

5. The method according to claim 4, wherein the specific T cells are cancer-specific T cells.

6. The method according to claim 4, wherein the target cells in the step (d) are cancer cells, the specific antigen in the step (d) is a cancer antigen, the dendritic killer cells presenting the specific antigen in the step (e) and (f) are the dendritic killer cells presenting the cancer antigen, the cell population of T cells in the step (f) are a cell population of $CD8^+$ T cells, and the specific T cells in the step (g) are cancer antigen-specific $CD8^+$ T cells.

7. The method according to claim 6, wherein the cancer cells, the dendritic killer cells, and the cell population of $CD8^+$ T cells are obtained from a cancer patient.

8. The method according to claim 3, wherein in the step (d), the target cells and the dendritic killer cells are both obtained from a cancer patient.

9. The method according to claim 1, wherein in the step (b), the concentration of IL-15 is 10 ng/mL, or the concentration of IL-12 is 2 ng/mL.

10. The method according to claim 1, wherein in the step (e), the dendritic killer cells presenting the specific antigen are capable of activating specific $CD8^+$ T cells.

11. The method according to claim 1, wherein the T cells in the step (f) are isolated $CD8^+$ T cells, and the specific T cells in the step (g) are specific $CD8^+$ T cells.

12. The method according to claim 1, wherein in the step (f) and (g), the cell population of T cells is activated by the dendritic killer cells presenting the specific antigen to form the specific T cells.

13. The method according to claim 1, wherein the target cells, the dendritic killer cells, and the cell population of T cells are obtained from a cancer patient.

14. A cancer treatment method for a human subject in need thereof, the method comprising the following steps:
(A) preparing a plurality of cancer antigen-specific $CD8^+$ T cells, comprising the following steps:
  (a") obtaining human peripheral blood mononuclear cells from the human subject;
  (b") culturing the cells with IL-15 and 0.5-20 ng/mL IL-12;
  (c") sorting dendritic killer cells, wherein the dendritic killer cells are cells with the cell surface marker $HLA-G^-CD14^-CD19^-CD3^-CD56^+HLA-D12^+$;
  (d") co-culturing the dendritic killer cells with a plurality of cancer cells obtained from the human subject, wherein the cancer cells express a cancer antigen;
  (e") harvesting the dendritic killer cells presenting the cancer antigen;
  (f") mixing the dendritic killer cells presenting the cancer antigen with a cell population of $CD8^+$ T cells obtained from the human subject and co-culturing for a period; and
  (g") harvesting a plurality of cancer antigen-specific $CD8^+$ T cells; and
(B) delivering the cancer antigen-specific $CD8^+$ T cells to the human subject.

* * * * *

UNITED STATES PATENT AND TRADEMARK OFFICE
CERTIFICATE OF CORRECTION

Page 1 of 1

PATENT NO. : 9,597,383 B2
APPLICATION NO. : 14/870961
DATED : March 21, 2017
INVENTOR(S) : Lee et al.

It is certified that error appears in the above-identified patent and that said Letters Patent is hereby corrected as shown below:

On the Title Page

Item (72) Add Inventor:
Nan-Shih Liao
No.128 Academia Road,
Section 2, Nankang, Taipei 11529, Taiwan Signed and Sealed this
Sixth Day of November, 2018

Andrei Iancu
*Director of the United States Patent and Trademark Office*